United States Patent
Robertson

(10) Patent No.: US 8,734,371 B2
(45) Date of Patent: May 27, 2014

(54) TWO-STRAP ANKLE BRACE WITH NON-RIGID BRACE BODY AND SEMI-RIGID ORTHOTIC ARCH SUPPORT

(75) Inventor: Eddy Leonard Robertson, Colton, WA (US)

(73) Assignee: Eddy Leonard Robertson, Colton, WA (US)

( * ) Notice: Subject to any disclaimer, the term of this patent is extended or adjusted under 35 U.S.C. 154(b) by 268 days.

(21) Appl. No.: 13/226,268

(22) Filed: Sep. 6, 2011

(65) Prior Publication Data

US 2012/0078152 A1    Mar. 29, 2012

Related U.S. Application Data

(60) Provisional application No. 61/386,225, filed on Sep. 24, 2010.

(51) Int. Cl.
- *A61F 5/37* (2006.01)
- *A61F 13/00* (2006.01)
- *A61B 19/00* (2006.01)
- *A61F 5/00* (2006.01)
- *A61F 13/06* (2006.01)

(52) U.S. Cl.
USPC .............. 602/27; 128/846; 128/869; 128/882; 602/5; 602/23; 602/60; 602/61; 602/62; 602/65

(58) Field of Classification Search
USPC ........ 602/5, 23, 27, 60–62, 65; 128/846, 869, 128/882
See application file for complete search history.

(56) References Cited

U.S. PATENT DOCUMENTS

2009/0192428 A1 * 7/2009 DeBoer et al. .................. 602/27

* cited by examiner

*Primary Examiner* — Patricia Bianco
*Assistant Examiner* — Brandon L Jackson
(74) *Attorney, Agent, or Firm* — Lee & Hayes, PLLC; Benjamin A. Keim

(57) ABSTRACT

An ankle brace is configured with a lateral anterior talofibular (ATF) strap and an inversion control strap affixed to a non-rigid brace body coupled to a semi-rigid orthotic arch support. The brace may be quickly donned and doffed by a wearer, and provides prophylactic or post-injury support to the ATF ligament without unduly restricting the wearer's motion. As a result, the wearer may participate in physical activity without significant impairment in range of motion.

19 Claims, 6 Drawing Sheets

TWO-STRAP ANKLE BRACE WITH NON-RIGID BRACE BODY AND SEMI-RIGID ORTHOTIC ARCH SUPPORT

PRIORITY

This application claims priority to U.S. Provisional Application Ser. No. 61/386,225, filed on Sep. 24, 2010, entitled "Two-Strap Ankle Brace with Non-Rigid Brace Body and Semi-Rigid Orthotic Arch Support" to Eddy Robertson. This pending provisional application is hereby incorporated by reference in its entirety, and the benefit of the filing date of this pending application is claimed to the fullest extent permitted.

BACKGROUND

Many forms of activity may result in injury to ligaments within a human ankle. The inversion ankle sprain is the single most common sports injury. Within the ankle, an anterior talofibular (ATF) ligament is commonly sprained and most severely injured. Pain and swelling related to this injury limits function and delays return to activity.

Traditional remedies for an ankle sprain have included a variety of taping techniques for the ankle. However, such taping requires the skill and care of a trained individual for application, and even with such skill and care, taping techniques offer marginal support and may cause damage to other portions of the foot may occur. For example, taping may transfer undue loads onto the shaft of the $5^{th}$ metatarsal, resulting in fractures. As an alternative to taping, braces with rigid sides or stiffeners have been offered. However, these braces suffer serious drawbacks including user discomfort, bulk, marginal support or prevention of re-injury, unduly limited range of motion, difficulty in donning, cost, and so forth.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Described in this disclosure is a two-strap ankle brace (brace) with a non-rigid brace body and techniques for donning and producing such a brace. As described in more depth below, this brace comprises a non-rigid brace body coupled to a semi-rigid orthotic arch support which in one implementation extends from the heel proximate to one or more of the metatarsal heads of a wearer's foot. Two straps, a lateral anterior talofibular (ATF) strap and an inversion control strap work in conjunction with the arch support as described below to control motion of the wearer's ankle. This control prevents excessive stretching of the ATF ligament, while still permitting the wearer functional range of motion of the ankle. The brace may be worn prophylactically to avoid injury or used post-injury to allow the wearer to resume activity. The light weight, low profile, and minimal restriction of motion allows the wearer to use the brace while also wearing other footwear, including cleats or other athletic shoes.

Physical Arrangement of the Brace

FIGS. 1-4 depict a series of views of the two-strap ankle brace with a non-rigid brace body and orthotic arch support as configured on a wearer's right foot as rotated around a vertical axis. While these views depict a right foot, it is understood that the braces and techniques described herein may be applied to a left foot as well. Within this disclosure specific materials are mentioned with regards to the brace by way of illustration only, and not as a limitation.

Figure 1:
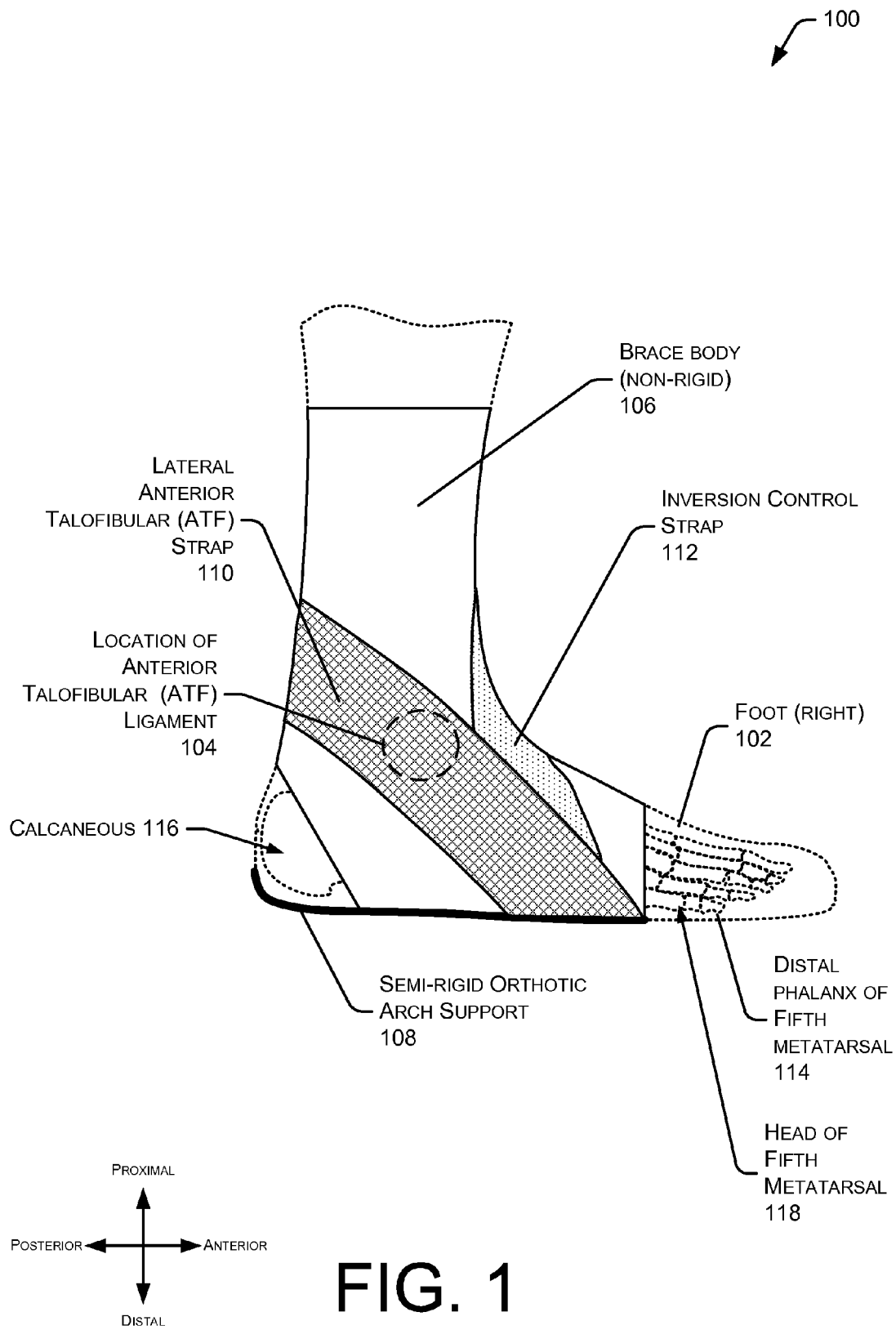
FIG. 1 is a medial view of a two-strap ankle brace with a non-rigid brace body as configured on a wearer's right foot.

FIG. 1 is a medial view 100 of the two-strap ankle brace. The ankle brace is depicted as worn on a human right foot 102, but in other implementations may be mirrored for use on a human left foot.

Within a human ankle an anterior talofibular (ATF) ligament passes from an anterior margin of the fibular malleolus anteriorly and medially to a talus bone anterior of the lateral articular facet. The general location of the ATF ligament is indicated by a broken circle 104.

A brace body 106 is shown. In one implementation, the brace body 106 is configured to maintain the wearer's foot and ankle a neutral configuration of about 90 degrees. The brace body 106 is non-rigid, and is thus substantially flexible. The brace body 106 may comprise canvas, polyester, nylon, cotton, or other flexible but non-rigid material. The non-rigid material may be woven, formed as a sheet, a composite, and so forth. The brace body 106 may be configured to cover the wearer's foot 102, or may be configured to leave at least a portion of the wearer's toes and heal exposed. These openings may provide several benefits, including but not limited to improving wearer comfort by improving airflow, minimizing chafing, and so forth. The brace body 106 may be lined. Such lining may provide several benefits, including improving wearer comfort, managing perspiration, and so forth. The liner may be integral or in some implementations removable. For example, the removable liner may be used to provide for easier cleaning.

Coupled to the brace body 106 is a semi-rigid orthotic arch support (or "arch support") 108. In the implementation shown here, the arch support 108 is configured to extend from a heel of the wearer's foot 102 proximate to, but not under, the metatarsal heads of the wearer's foot 102. For example, the arch support 108 may extend from the heel anteriorly beneath the shafts of the metatarsals. For the purposes of this application, "proximate" is used to designate that features are close by or in contact with one another, while "proximal" is used to indicate a direction relative to the anatomy of the wearer.

The arch support 108 generally conforms to a plantar surface of the foot 102, providing some support to the wearer's longitudinal arch. In another implementation, the arch support 108 may be configured to extend from a heel of the wearer's foot 102 proximate to, or past, the metatarsal heads of the wearer's foot 102.

The brace body 106 may be coupled to the arch support 108 either permanently or removably. For example, the arch support 108 may be permanently coupled via sewing, gluing, laminating, and so forth. In other implementations, the arch support 108 may be removably coupled to the brace body with snaps, hook and loop fasteners, clips, and so forth. In some implementations, a lower portion of the brace body 106 may be modified to form the semi-rigid orthotic arch support 108. For example, the lower portion of the brace body may be impregnated with a resin which is solidified to form the arch support 108.

In some implementations, the arch support 108 may be configured to act as an orthotic to support contours of the foot 102. This may be a generalized orthotic suitable for a typical human foot, or a specialized custom orthotic designed for a particular wearer. The arch support 108 may be configured to provide a neutral base contour to the wearer's foot.

The arch support 108 may comprise a semi-rigid material, such as a polymer, metal, carbon fiber, fiberglass, composite material, or combination thereof. The composition, and in some implementations thickness, of the arch support 108 may be tailored to provide a pre-determined amount of flexure in the arch support 108. This amount of flexure may be selected to account for the wearer's weight, gait, or other physical factors.

A lateral ATF strap 110 is coupled to an anterior portion of the arch support 108, the brace body, or both, proximate to a lateral-distal margin of the brace body 106. The lateral ATF strap 110 serves, at least in part, to limit the motion of the forefoot in plantarflexion, inversion, and adduction. This coupling may be permanent or removable. The lateral ATF strap 110 is configured such that, when worn, the strap passes over a surface of the brace body 106 proximate to the ATF ligament 104. In some implementations, the lateral ATF strap 110 may be coupled to a position proximate to a lateral malleolus of the wearer. For example, a hook and loop fastener may be used to join the lateral strap 110 to the brace body 106 in this area proximate to the lateral malleolus.

A first end of the ATF strap 110 is coupled to the arch support 108 or the brace body 106 at a lateral-distal margin of the brace body 106. The lateral ATF strap 110 passes over a surface of the brace body 106 proximate to at least a portion of the ATF ligament 104 when worn by a wearer, and wraps around a posterior portion of the ankle, proximal to the calcaneous bone. Once wrapped around, a second end of the ATF strap 110 is coupled to a proximal-medial portion of the brace body 106, another member of the brace such as the inversion control strap 112 described below, or a combination thereof.

An inversion control strap 112 is also present on the brace. The inversion control strap 112, among other functions, controls inversion of the foot, limiting movement of a plantar surface of the foot 102 medially. A first end of the inversion control strap 112 couples to the lateral ATF strap 110 proximate to a mid-tarsal joint of the wearer. This coupling may be permanent or removable. In some implementations, the inversion control strap 112 may couple to the brace body 206, as well as, or in addition to, the lateral ATF strap 110.

The inversion control strap 112 is configured to pass over the surface of the brace body 106 medially anterior to the ankle joint when worn by the wearer. A second end of the inversion control strap 112 couples proximate to the second end of the ATF strap 110, and is shown in more detail below with regards to FIG. 3. The second end of the inversion control strap 112 may couple to the second end of the ATF strap 110, to the brace body, or both.

The straps, such as the lateral ATF strap 110 and the inversion control strap 112 may be substantially non-elastic under the usage described herein. For example, in one implementation the straps may comprise nylon webbing. In other implementations, the straps may be elastic. By using the straps in conjunction with the arch support 108, force on the straps during movement of the foot 102 is distributed across the entire foot 102, reducing or eliminating the possibility of metatarsal breaks, such as may occur with conventional taping.

For reference in positioning, and not by way of limitation, some of the bones of the foot 102 are depicted. In particular, a distal phalanx of a fifth metatarsal 114 is shown, as well as a portion of a calcaneous 116, and a head of the fifth metatarsal 118.

Figure 2:
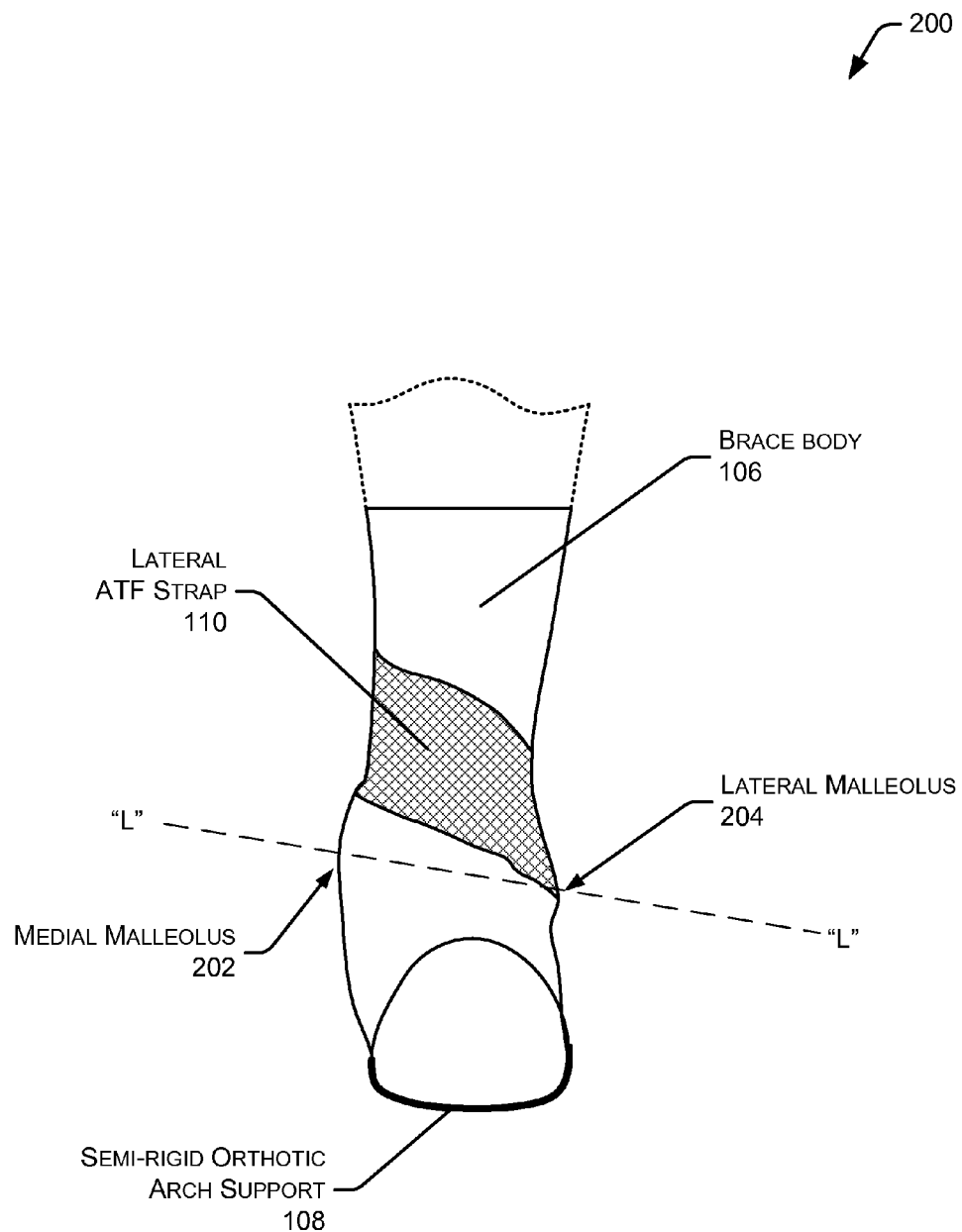
FIG. 2 is an anterior view of the brace of FIG. 1.

FIG. 2 is an anterior view 200 of the brace. In this view, the wearer's medial malleolus 202 and lateral malleolus 204 are shown. As seen here, the lateral ATF strap 110 passes around the posterior portion of the wearer's ankle, generally proximal (or superior) to a line "L" extending from the medial malleolus 202 through the lateral malleolus 204.

Figure 3:
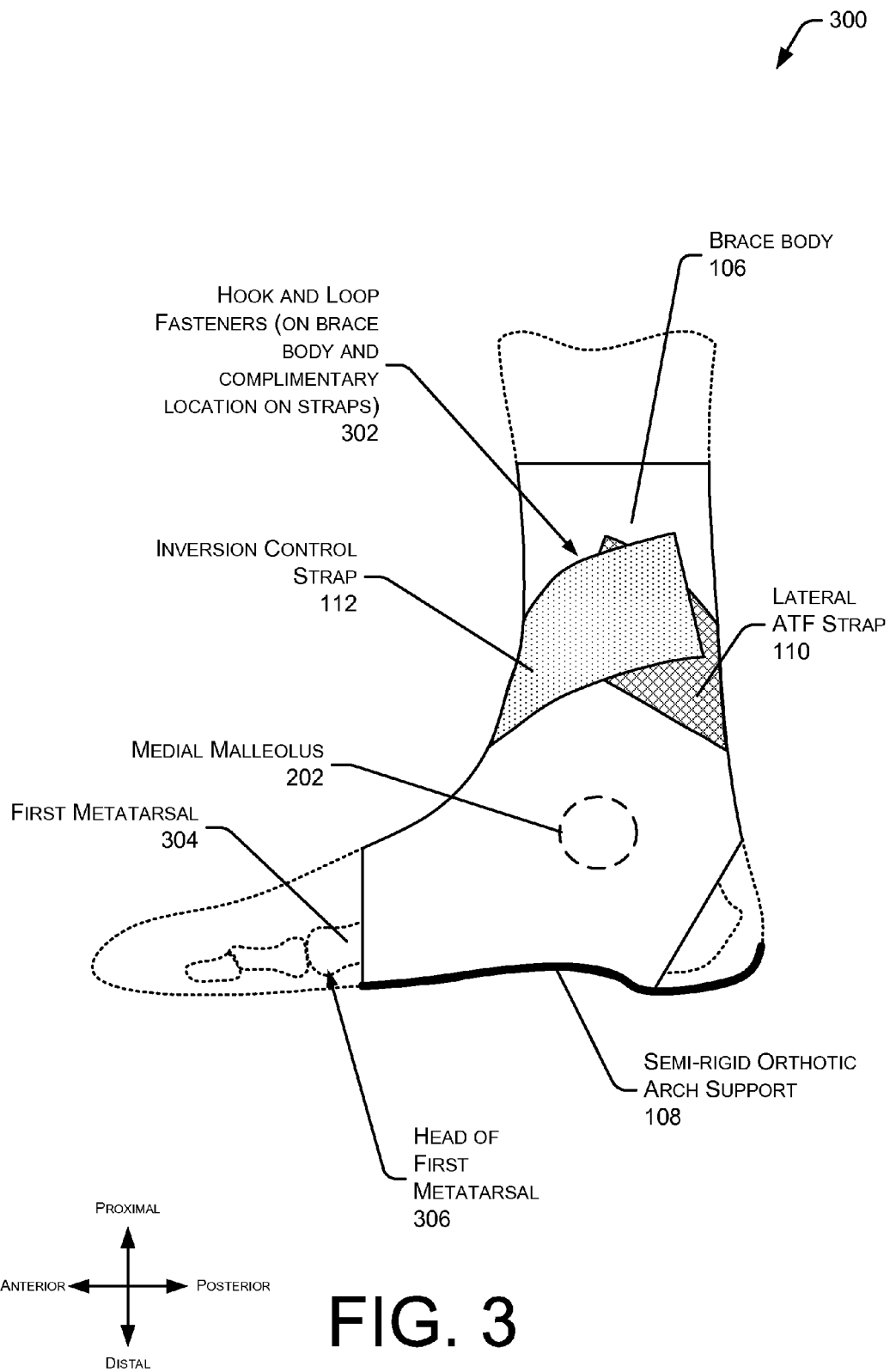
FIG. 3 is a lateral view of the brace of FIG. 1.

FIG. 3 is a lateral view 300 of the brace. In this view, the second end of the lateral ATF strap 110 is depicted terminating at a proximal medial portion of the brace body 106. As described above, the lateral ATF strap 110 may couple removably to the brace body 106 such as with a hook and loop fastener as shown at 302. Also shown in this view is the second end of the inversion control strap 112, which also terminates at the proximal medial portion of the brace body 106 coincident with the second end of the lateral ATF strap 110. As above, the inversion control strap 112 may couple to the brace body 106 via a removable fasteners, such as shown at 302.

For reference in positioning, and not by way of limitation some anatomy of the wearer's foot 102 is depicted. As seen here, the medial malleolus 202 is indicated, as well as the first metatarsal 304 of the wearer's foot 102, and a head of the first metatarsal 306. As described above and as shown here in one implementation, the arch support 108 extends from the heel proximate to, but not under, the head of the metatarsals, including the head of the first metatarsal 306.

Figure 4:
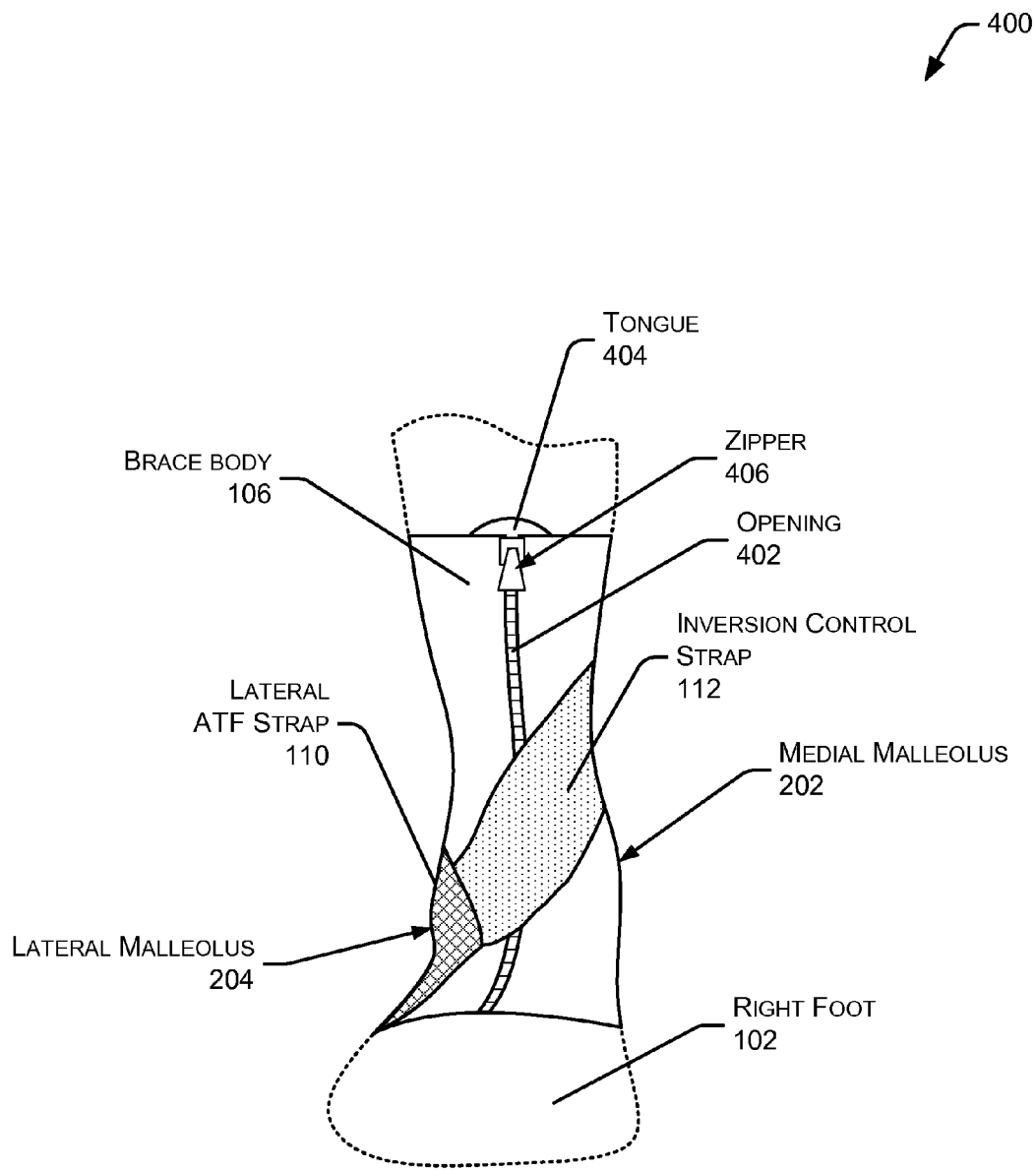
FIG. 4 is a posterior view of the brace of FIG. 1.
Figure 4:
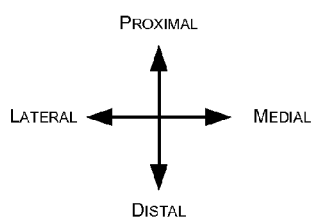

FIG. 4 is a posterior view 400 of the brace. In this view, the coupling of the lateral ATF strap 110 and the inversion control strap 112 is visible. Also shown is an opening 402 which may be present in some implementations. The opening 402 is configured to permit a wearer to don and doff the brace. For example, when the brace body 106 comprises a non-elastic material such as canvas, the opening 402 allows the user to insert or remove a foot. As shown here, the opening 402 is configured along the anterior surface of the brace body 106. In other implementations the opening 402 may be configured along one or more other surfaces of the brace body 106.

A tongue 404 behind the opening 402 may also be present. The opening 402 may be secured closed while the brace is in use to maintain the brace's position on the wearer's foot. For example, a zipper 406 may close the opening as shown here. In other implementations, laces, hook and loop fasteners, clasps, and so forth may be used. In yet another implementation, elastomeric material may be interposed between the edges of the opening 402 such that pull from the elastomeric material maintains the opening 402 in a substantially closed condition while in use, yet configured to expand to allow easy donning and doffing of the brace.

Processes of Donning and Manufacturing the Brace

The following processes are illustrated as a collection of blocks in a logical flow graph, which represent a sequence of operations that can be implemented manually, by automated machinery, or a combination thereof. The order in which the operations are described is not intended to be construed as a limitation, and any number of the described blocks can be combined in any order and/or in parallel to implement the process. For discussion purposes, the following processes are described with reference to the brace of FIGS. 1-4.

Figure 5:
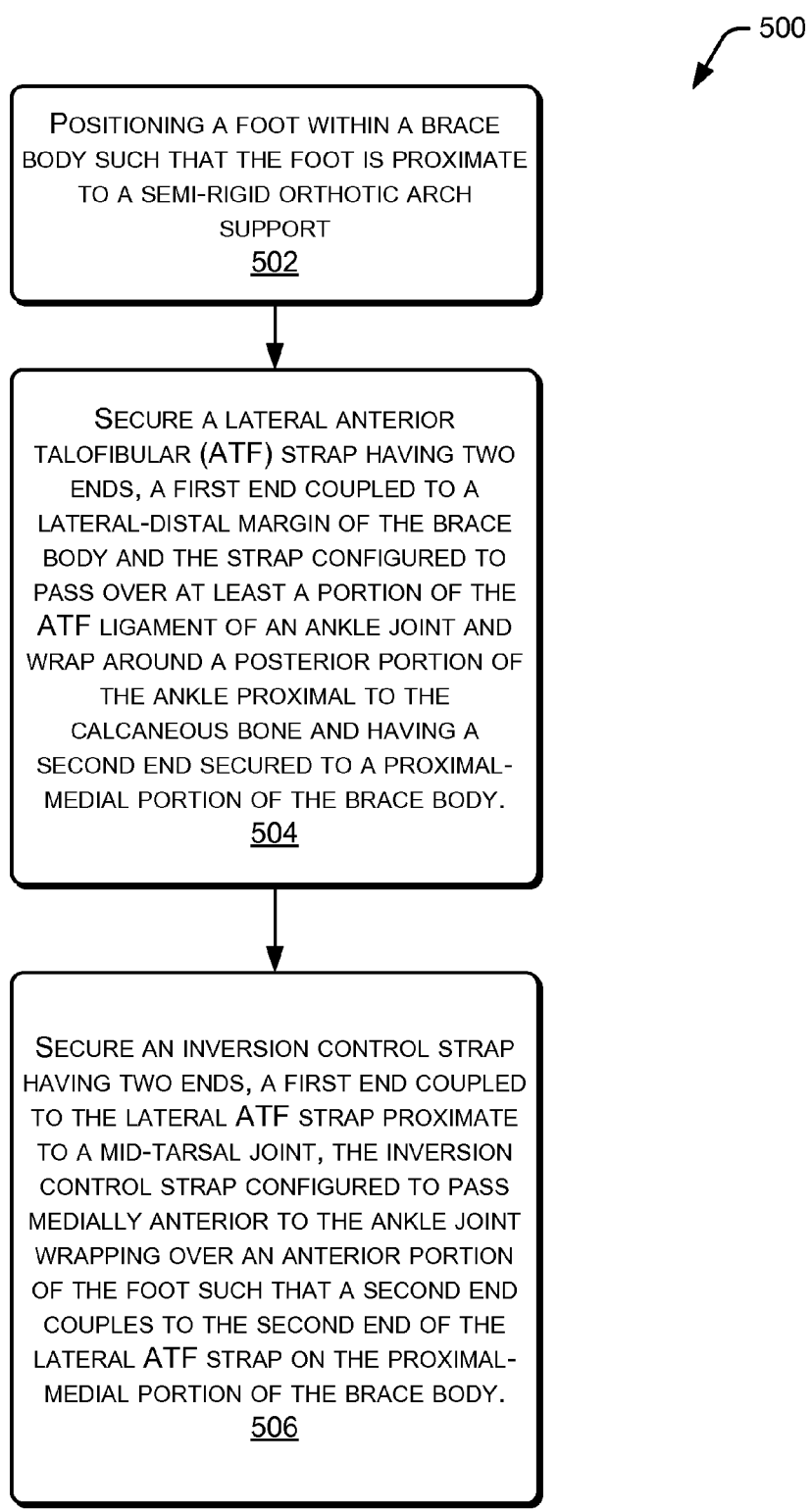
FIG. 5 is a flow diagram of an illustrative process of donning the brace.

FIG. 5 is a flow diagram of an illustrative process 500 of donning the brace. At 502, the foot 102 is positioned within the brace body 106 such that a plantar surface of the wearer's foot is proximate to and coincident with the semi-rigid orthotic arch support 108.

At 504, the lateral ATF strap 110 is secured. When secured, a first end of the ATF strap 110 is coupled to an anterior portion of the arch support 108, the brace body 106, or both at a lateral-distal margin of the brace body 106. The lateral ATF strap 110 is configured such that a body of the strap passes over a surface of the brace body 106 proximate to at least a portion of an ATF ligament 104 when worn by a wearer, and wraps around a posterior portion of the ankle, proximal to the calcaneous bone. Once wrapped around, a second end of the ATF strap 110 is coupled to a proximal-medial portion of the brace body 106.

At 506, the inversion control strap 112 is secured. A first end of the inversion control strap 112 is coupled to the lateral ATF strap 110 proximate to a mid-tarsal joint. A body of the inversion control strap 112 is configured to pass medially anterior to the ankle joint, wrapping over an anterior portion of the foot. A second end of the inversion control strap 112 couples to a position proximate to the second end of the ATF strap 110 on the proximal-medial portion of the brace body.

Figure 6:
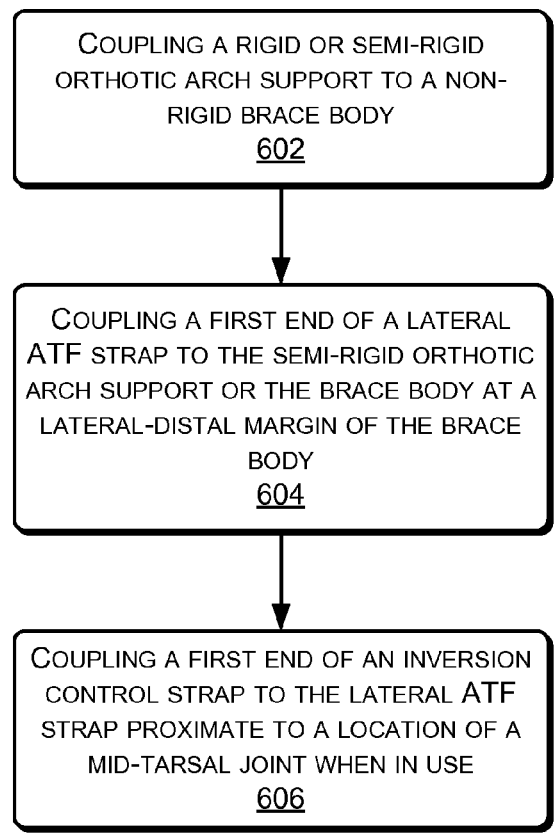
FIG. 6 is a flow diagram of an illustrative process of manufacturing the brace.

FIG. 6 is a flow diagram of an illustrative process 600 of manufacturing the brace. At 602, the semi-rigid orthotic arch support 108 is coupled to a non-rigid brace body 106. This coupling may comprise sewing, adhering, or laminating, and so forth. In another implementation, the coupling may comprise altering or impregnating at least a portion of a bottom portion of the brace body 106 such that it becomes semi-rigid, forming an integral arch support 108.

At 604, a first end of the lateral ATF strap 110 is coupled to an anterior portion of the arch support 108 or the brace body 106 at a lateral-distal margin of the brace body 106. This coupling may be permanent such as with an adhesive, sewing, and so forth, or removable such as with snaps, hook and loop fasteners, and so forth. In another implementation, a pocket within the brace body 106 may hold the arch support 108.

As described above, the lateral ATF strap 110 is configured to, when worn by the wearer, pass over a surface of the brace body 106 proximate to at least a portion of an ATF ligament 104 of an ankle joint and couple at a second end of the ATF strap 110 to a proximal-medial portion of the brace body 106. In some implementations, the lateral ATF strap 110 is further configured to couple to the brace body 106 at a position proximate to the lateral malleolus 204 when worn.

At 606, a first end of the inversion control strap 112 is coupled to the portion of the lateral ATF strap 110 proximate to a location of a mid-tarsal joint of the wearer. This coupling may be permanent such as with an adhesive or sewing, and so forth or removable such as with snaps, hook and loop fasteners, and so forth.

As described above, the inversion control strap 112 is configured to, when worn by the wearer, pass over a surface of the brace body 106 medially anterior to the ankle joint and couple at a second end of the inversion control strap 112 to the ATF strap 110.

In other implementations the brace may be incorporated into a shoe or sandal. This would provide protection to the wearer's foot while also preventing damage to the ATF ligament.

Although specific details of illustrative processes are described with regard to the figures and other flow diagrams presented herein, it should be understood that certain acts shown in the figures need not be performed in the order described, and may be modified, and/or may be omitted entirely, depending on the circumstances.

What is claimed is:

1. A brace comprising:
   a semi-rigid orthotic arch support configured to extend from a heel of a wearer proximate to one or more of the metatarsal heads of the wearer;
   a non-rigid brace body coupled to the semi-rigid orthotic arch support;
   a lateral anterior talofibular (ATF) strap configured to:
      couple a first end to an anterior portion of the semi-rigid orthotic arch support, the brace body, or both at a lateral-distal margin of the brace body proximate to the semi-rigid orthotic arch support;
      pass over a surface of the brace body proximate to at least a portion of an ATF ligament of an ankle joint when worn by a wearer;
      couple removably a second end to a proximal-medial portion of the brace body; and
   an inversion control strap configured to:
      couple a first end to the lateral ATF strap proximate to a mid-tarsal joint when worn by the wearer;
      pass over a surface of the brace body medially anterior to the ankle joint when worn by the wearer;
      couple removeably a second end to the second end of the ATF strap.

2. The brace of claim 1, wherein the removable couplings comprise hook and loop fasteners.

3. The brace of claim 1, wherein the lateral ATF strap and the inversion control strap comprise a substantially non-elastic material.

4. The brace of claim 1, wherein the semi-rigid orthotic arch support comprises semi-rigid polymer.

5. The brace of claim 1, wherein the brace body comprises an opening configured to permit a wearer to don and doff the brace.

6. The brace of claim 5, wherein the opening is configured to close with at least one of a fastener, the fastener comprising a hook and loop fastener, a zipper, or one or more laces.

7. The brace of claim 1, wherein the lateral ATF strap is further configured to removeably couple to the brace body at a position proximate to a lateral malleolus when worn by the wearer.

8. The brace of claim 1, wherein the brace body comprises a non-elastic material.

9. A method comprising:
   positioning a foot within a brace body comprising non-rigid material such that the foot is proximate to a semi-rigid orthotic arch support coupled to the brace body;
   securing a lateral anterior talofibular (ATF) strap such that:
      a first end couples to a lateral-distal margin of the brace body proximate to the arch support;
      a body of the strap passes over a surface of the brace body proximate to at least a portion of an ATF ligament of an ankle joint when worn by a wearer;
      a second end couples to a proximal-medial portion of the brace body; and
   securing an inversion control strap such that:
      a first end couples to the lateral ATF strap proximate to a mid-tarsal joint when worn by the wearer;
      a body of the strap passes over a surface of the brace body medially anterior to the ankle joint when worn by the wearer;
      a second end couples to the second end of the lateral ATF strap.

10. The method of claim 9, further comprising opening an opening within the brace body, wherein the opening is configured to allow the wearer to insert or remove a foot.

11. The method of claim 9, wherein the arch support is configured to extend from a heel of the wearer proximate to a plurality of metatarsal heads of the wearer's foot.

12. The method of claim 9, further comprising closing an opening within the brace body, wherein the opening is configured to allow the wearer to insert or remove a foot.

13. The method of claim 9, wherein the coupling of the first end of the lateral ATF strap to the lateral-distal margin of the brace body comprises a non-removable fastening.

14. The method of claim 9, wherein the coupling of the first end of the inversion control strap to the lateral ATF strap proximate to the mid-tarsal joint comprises a non-removable fastening.

15. A method comprising:
coupling an arch support to a non-rigid brace body;
coupling a first end of a lateral anterior talofibular (ATF) strap to the arch support, the brace body, or both at a lateral-distal margin of the brace body, wherein the lateral ATF strap is further configured to, when worn by a wearer:
 pass over a surface of the brace body proximate to at least a portion of an ATF ligament of an ankle joint; and
 couple at a second end of the ATF strap to a proximal-medial portion of the brace body; and
coupling a first end of an inversion control strap to the arch support or the brace body proximate to a location of a mid-tarsal joint of the wearer when worn by the wearer.

16. The method of claim 15, wherein the arch support comprises a semi-rigid orthotic.

17. The method of claim 15, wherein the lateral ATF strap is further configured to couple to the brace body at a position proximate to a lateral malleolus when worn by the wearer.

18. The method of claim 15, wherein the inversion control strap is further configured to, when worn by the wearer:
pass over a surface of the brace body medially anterior to an ankle joint;
couple at a second end of the inversion control strap to the ATF strap.

19. The method of claim 15, wherein the coupling comprises sewing, adhering, or laminating.

* * * * *